(12) United States Patent
Gao et al.

(10) Patent No.: US 8,059,886 B2
(45) Date of Patent: Nov. 15, 2011

(54) ADAPTIVE SIGNATURE DETECTION

(75) Inventors: Yong Gao, Fremont, CA (US); Junqing Huang, Fremont, CA (US); Lisheng Gao, Morgan Hill, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/119,542

(22) PCT Filed: May 28, 2010

(86) PCT No.: PCT/US2010/036514
§ 371 (c)(1),
(2), (4) Date: Mar. 17, 2011

(87) PCT Pub. No.: WO2010/141337
PCT Pub. Date: Dec. 9, 2010

(65) Prior Publication Data
US 2011/0170766 A1    Jul. 14, 2011

Related U.S. Application Data

(60) Provisional application No. 61/183,966, filed on Jun. 3, 2009.

(51) Int. Cl.
*G06K 9/00* (2006.01)
(52) U.S. Cl. ........................................ 382/149
(58) Field of Classification Search ............... 382/141, 382/149, 168, 173, 209, 218, 225; 348/92, 348/125–126
See application file for complete search history.

(56) References Cited

U.S. PATENT DOCUMENTS

| | | | |
|---|---|---|---|
| 6,504,948 B1 * | 1/2003 | Schemmel et al. | ........... 382/149 |
| 7,315,363 B2 * | 1/2008 | Hamamatsu et al. | ...... 356/237.2 |
| 2002/0054694 A1 | 5/2002 | Vachtsevanos et al. | |
| 2006/0071081 A1 | 4/2006 | Wang | |
| 2006/0199287 A1 | 9/2006 | Fu et al. | |
| 2006/0273242 A1 | 12/2006 | Hunsche | |
| 2008/0055591 A1 | 3/2008 | Walton | |
| 2008/0317339 A1 | 12/2008 | Steinberg et al. | |

* cited by examiner

*Primary Examiner* — Daniel Mariam
(74) *Attorney, Agent, or Firm* — Luedeka, Neely & Graham, P.C.

(57) ABSTRACT

A processor-based method for detecting defects in an integrated circuit, by creating an image of at least a portion of the integrated circuit with a sensor, grouping pixels of the image into bins based at least in part on a common characteristic of the pixels that are grouped within a given bin, creating a histogram of the pixels in each of the bins, calculating a mean value of the histogram for each of the bins, comparing the mean value for each of the bins to a threshold value, flagging as defect candidates those bins where the mean value of the bin varies from the threshold value by more than a predetermined amount, and performing signature detection on the bins that are flagged as defect candidates, where the image of the integrated circuit is not directly compared to any other image of an integrated circuit.

17 Claims, 1 Drawing Sheet

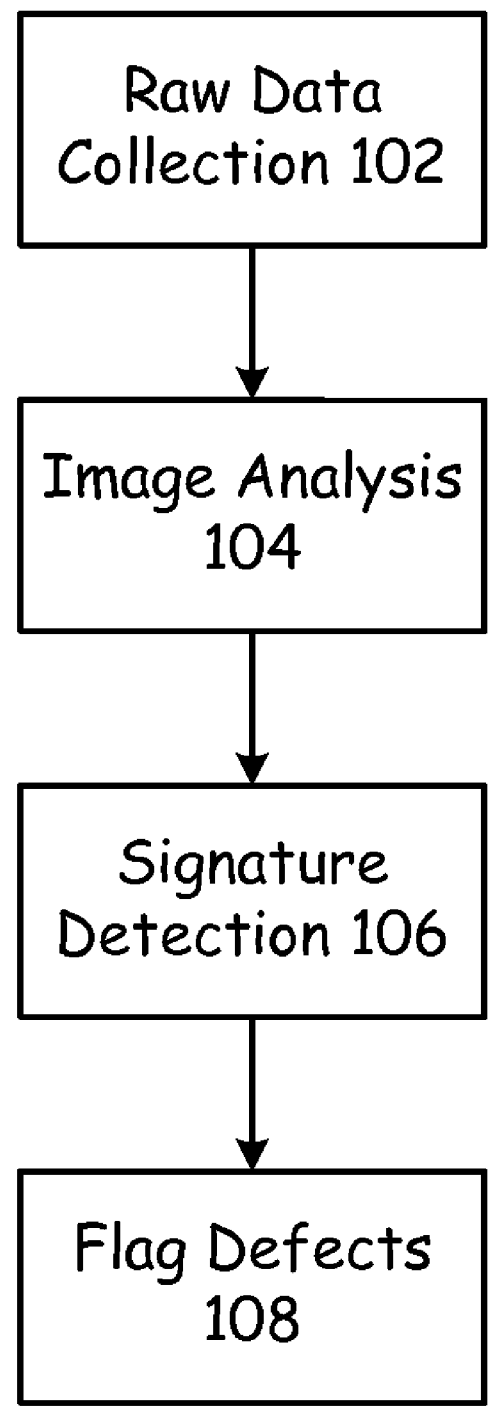

ADAPTIVE SIGNATURE DETECTION

RELATED APPLICATIONS

This application claims all rights and priority on prior pending U.S. provisional patent application Ser. No. 61/183,966 filed 2009.06.03 and PCT patent application serial number US2010/036514 filed 2010.05.28. This invention relates to the field of integrated circuit. More particularly, this invention relates to optical inspection of integrated circuits.

BACKGROUND OF THE INVENTION

An inspection, be it optical or electron beam, is typically performed at many different times during the fabrication cycle of a modern integrated circuit. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

The inspection of integrated circuits is typically accomplished using a comparison process, where information from the image of a test die is compared to information from the image of a reference die. These two information sets are subtracted, one from the other, to yield a difference set. Because the test die and the reference die are assumed to be identical, any non-zero values in the difference set are assumed to be the result of defects on either the test die or the reference die.

In some inspection routines, the reference die is an absolute reference that is known to be non-defective. In this case, any non-zero values are properly attributable to defects in the test die. In other inspection routines the reference die is a floating reference, such as another die on the same substrate as the test die. In this case, the non-zero values in the difference set might be attributable to either the test die or the reference die, and further investigation is required.

However, in some cases the floating reference die and the test die both have a defect in the same location on each die. When this occurs, a subtraction of the information from the two images yields a zero value in the position within the difference set that indicates the location of the two defects. However, zero values are interpreted as no defect, rather than a matching defect on both of the dice.

What is needed, therefore, is an inspection system that overcomes problems such as those described above, at least in part.

SUMMARY OF THE INVENTION

The above and other needs are met by a processor-based method for detecting defects in an integrated circuit, by creating an image of at least a portion of the integrated circuit with a sensor, grouping pixels of the image into bins based at least in part on a common characteristic of the pixels that are grouped within a given bin, creating a histogram of the pixels in each of the bins, calculating a mean value of the histogram for each of the bins, comparing the mean value for each of the bins to a threshold value, flagging as defect candidates those bins where the mean value of the bin varies from the threshold value by more than a predetermined amount, and performing signature detection on the bins that are flagged as defect candidates, where the image of the integrated circuit is not directly compared to any other image of an integrated circuit.

In this manner, a defect detection routine is performed on the integrated circuit, which routine does not rely upon the comparison of the image of a test die to the image of a reference die. Therefore, the case where defects are overlooked because they exist on adjacent or near-neighbor dice is eliminated in the embodiments of the present invention. This is very valuable for detecting defects such as under-polish, pattern shift, gross defects that affect more than one die, process induced variations, and so forth.

In various embodiments according to this aspect of the invention, the common characteristic is at least one of intensity, gradient, texture, projection along the x axis, projection along the y axis, location, range of pixel in the neighborhood, maximum value in the neighborhood, and minimum value in the neighborhood. In some embodiments the sensor comprises at least one of a camera, a charge coupled device, a time domain and integration device, an electron beam microscope, a bright field microscope, a dark field microscope, and a surfscan. In some embodiments the histogram is created based on the intensity of the pixels in the bin. In some embodiments the signature detection includes at least one of under-polish, pattern shift, gross defects that affect more than one integrated circuit, and process-induced variations.

According to another aspect of the present invention there is described an apparatus for detecting defects in an integrated circuit, the apparatus having a sensor for creating an image of at least a portion of the integrated circuit. A processor groups pixels of the image into bins based at least in part on a common characteristic of the pixels that are grouped within a given bin, creates a histogram of the pixels in each of the bins, calculates a mean value of the histogram for each of the bins, compares the mean value for each of the bins to a threshold value, flags as defect candidates those bins where the mean value of the bin varies from the threshold value by more than a predetermined amount, and performs signature detection on the bins that are flagged as defect candidates. The image of the integrated circuit is not directly compared to any other image of an integrated circuit. A display presents results of at least the signature detection process.

According to yet another aspect of the present invention there is described a processor-based method for detecting defects in an integrated circuit by creating an image of at least a portion of the integrated circuit with a sensor, grouping pixels of the image into bins, calculating a mean value of a characteristic of the pixels in each bin, comparing the mean value for each of the bins to a threshold value, flagging as defect candidates those bins where the mean value of the bin varies from the threshold value by more than a predetermined amount, and performing signature detection on the bins that are flagged as defect candidates, where the image of the integrated circuit is not directly compared to any other image of an integrated circuit.

In various embodiments according to this aspect of the invention, the characteristic is at least one of intensity, gradient, texture, projection along the x axis, projection along the y axis, location, range of pixel in the neighborhood, maximum value in the neighborhood, and minimum value in the neighborhood. In some embodiments the sensor is at least one of a camera, a charge coupled device, a time domain and integration device, an electron beam microscope, a bright field microscope, a dark field microscope, and a surfscan. In some embodiments the signature detection includes at least one of under-polish, over-polish, pattern shift, gross defects that affect more than one integrated circuit, and process-induced variations. Some embodiments additionally include filtering the characteristic of the pixels prior to grouping the pixels into bins. Some embodiments additionally include filtering the characteristic of the pixels after grouping the pixels and prior to performing signature detection.

In various embodiments according to this aspect of the invention, the common characteristic is at least one of intensity, gradient, texture, projection along the x axis, projection along the y axis, location, range of pixel in the neighborhood, maximum value in the neighborhood, and minimum value in the neighborhood. In some embodiments the sensor comprises at least one of a camera, a charge coupled device, a time domain and integration device, an electron beam microscope, a bright field microscope, a dark field microscope, and a surfscan. In some embodiments the histogram is created based on the intensity of the pixels in the bin. In some embodiments the signature detection includes at least one of under-polish, pattern shift, gross defects that affect more than one integrated circuit, and process-induced variations.

BRIEF DESCRIPTION OF THE DRAWINGS

Further advantages of the invention are apparent by reference to the detailed description when considered in conjunction with the FIGURE, which is not to scale so as to more clearly show the details, wherein like reference numbers indicate like elements, and which depicts a flow chart of a method for detecting defects in a die, according to an embodiment of the present invention.

DETAIL DESCRIPTION OF THE DRAWING

With reference now to the FIGURE, there is depicted a flow chart of a processor-based method 100 according to an embodiment of the present invention. In step 102, raw image data is collected on only the test die—no reference die is imaged or used for this process. The image data is collected by a sensor, such as by a camera, CCD, TDI, electron beam microscope, bright field, dark field, surfscan, or some other device.

An analysis of the image is performed, as given in step 104. For each image frame collected in step 102, a segmentation process is performed, which groups together those pixels that share a common set of preselected properties, and places those pixels into different bins, according to the different sets of preselected properties associated with each bin. These properties can include, for example, intensity, gradient, texture, projection along the x axis, projection along the y axis, location, range of pixel in the neighborhood, maximum value in the neighborhood, minimum value in the neighborhood, design information, and so forth. Prior to the binning process, a preprocessing of the image can be accomplished, such as by applying a smoothing filter. Subsequent steps can be applied to the pixels of alternately the entire image frame, a specific region, or a specific segment. In some embodiments regions are drawn by the user, and segmentation is determined by an algorithm, such as by using projection in the x dimension. Region definitions can also be derived from the design data base.

For each bin, a histogram is calculated, such as based on the intensity of the pixels in the bin, or a transformation of the intensity of the pixel, or other characteristic of the pixel, such as neighborhood characteristics. The histogram can also be based on other properties, such as gradient. The intensity can be analog based or digital based. A transform can be performed on the intensity (or other used property) prior to producing the histogram. The histogram of some embodiments is two dimensional histogram, such as a histogram of intensity in one dimension, and a neighborhood-based property in the other dimension.

Once the histogram is formed, a mean value for the graphed characteristic (intensity in this example) is calculated. This mean value is compared to a threshold value. In one embodiment, the threshold is selected based on empirical data gathered from experiments on different sets of substrates, where the different sets represent normal conditions, below normal conditions, transition conditions, and excursion conditions. Raw images are collected on these substrates to identify the variation range. Based on the statistics of the data that is collected, a threshold is determined. If the mean value of the histogram for a given pixel group (bin) varies from the threshold by more than a predefined amount, then that pixel group is flagged as representing a possible defect. In another embodiment, a threshold is applied directly to the selected pixel characteristic or characteristics, without forming the histogram first. Those pixels that exceed the threshold are flagged as described in this paragraph as defect candidates.

For those dice that are indicated as defect candidates in step 104, a signature detection routine 106 is performed on the image data, wherein pixels within the bin that varied from the predefined histogram value as determined in step 104, are flagged as defective pixels. Prior to the signature detection routine 106, another processing step can be performed on the pixels, such as further filtering or binning.

In the final step 108, those die having defects are flagged as such.

In this manner, a defect detection routine is performed on the substrate, which routine does not rely upon the comparison of the image of a test die to the image of a reference die. Therefore, the case where defects are overlooked because they exist on adjacent or near-neighbor dice is eliminated in the embodiments of the present invention. This is very valuable for detecting defects such as under-polish, pattern shift, gross defects that affect more than one die, process induced variations, and so forth.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A processor-based method for detecting defects in an integrated circuit, the method comprising the steps of:

creating an image of at least a portion of the integrated circuit with a sensor, grouping pixels of the image into bins based at least in part on a common characteristic of the pixels that are grouped within a given bin, creating a histogram of the pixels in each of the bins, calculating a mean value of the histogram for each of the bins, comparing the mean value for each of the bins to a threshold value, flagging as defect candidates those bins where the mean value of the bin varies from the threshold value by more than a predetermined amount, and performing signature detection on the bins that are flagged as defect candidates, where the image of the integrated circuit is not directly compared to any other image of an integrated circuit.

2. The method of claim 1, wherein the common characteristic is at least one of intensity, gradient, texture, projection along the x axis, projection along the y axis, location, range of pixel in the neighborhood, maximum value in the neighborhood, and minimum value in the neighborhood.

3. The method of claim 1, wherein the sensor comprises at least one of a camera, a charge coupled device, a time domain and integration device, an electron beam microscope, a bright field microscope, a dark field microscope, and a surfscan.

4. The method of claim 1, wherein the histogram is created based on the intensity of the pixels in the bin.

5. The method of claim 1, wherein the signature detection includes at least one of under-polish, over-polish, pattern shift, gross defects that affect more than one integrated circuit, and process-induced variations.

6. A apparatus for detecting defects in an integrated circuit, comprising:

a sensor for creating an image of at least a portion of the integrated circuit, a processor for, grouping pixels of the image into bins based at least in part on a common characteristic of the pixels that are grouped within a given bin, creating a histogram of the pixels in each of the bins, calculating a mean value of the histogram for each of the bins, comparing the mean value for each of the bins to a threshold value, flagging as defect candidates those bins where the mean value of the bin varies from the threshold value by more than a predetermined amount, and performing signature detection on the bins that are flagged as defect candidates, where the image of the integrated circuit is not directly compared to any other image of an integrated circuit, and a display for presenting results of at least the signature detection process.

7. The apparatus of claim 6, wherein the common characteristic is at least one of intensity, gradient, texture, projection along the x axis, projection along the y axis, location, range of pixel in the neighborhood, maximum value in the neighborhood, and minimum value in the neighborhood.

8. The apparatus of claim 6, wherein the sensor comprises at least one of a camera, a charge coupled device, a time domain and integration device, an electron beam microscope, a bright field microscope, a dark field microscope, and a surfscan.

9. The apparatus of claim 6, wherein the histogram is created based on the intensity of the pixels in the bin.

10. The apparatus of claim 6, wherein the signature detection includes at least one of under-polish, pattern shift, gross defects that affect more than one integrated circuit, and process-induced variations.

11. A processor-based method for detecting defects in an integrated circuit, the method comprising the steps of:

creating an image of at least a portion of the integrated circuit with a sensor, grouping pixels of the image into bins, calculating a mean value of a characteristic of the pixels in each bin, comparing the mean value for each of the bins to a threshold value, flagging as defect candidates those bins where the mean value of the bin varies from the threshold value by more than a predetermined amount, and performing signature detection on the bins that are flagged as defect candidates, where the image of the integrated circuit is not directly compared to any other image of an integrated circuit.

12. The method of claim 11, wherein the pixels as grouped based upon at least one of common pixel characteristic, pixel segment, pixel region, and design data information.

13. The method of claim 11, wherein the characteristic is at least one of intensity, gradient, texture, projection along the x axis, projection along the y axis, location, range of pixel in the neighborhood, maximum value in the neighborhood, and minimum value in the neighborhood.

14. The method of claim 11, wherein the sensor comprises at least one of a camera, a charge coupled device, a time domain and integration device, an electron beam microscope, a bright field microscope, a dark field microscope, and a surfscan.

15. The method of claim 11, wherein the signature detection includes at least one of under-polish, over-polish, pattern shift, gross defects that affect more than one integrated circuit, and process-induced variations.

16. The method of claim 11, further comprising the step of filtering the characteristic of the pixels prior to grouping the pixels into bins.

17. The method of claim 11, further comprising the step of filtering the characteristic of the pixels after grouping the pixels and prior to performing signature detection.

* * * * *